(12) United States Patent
Cheronis et al.

(10) Patent No.: US 7,074,586 B1
(45) Date of Patent: Jul. 11, 2006

(54) QUANTITATIVE ASSAY FOR LOW ABUNDANCE MOLECULES

(75) Inventors: John C. Cheronis, Conifer, CO (US); David Trollinger, Boulder, CO (US)

(73) Assignee: Source Precision Medicine, Inc., Boulder, CO (US)

( * ) Notice: Subject to any disclaimer, the term of this patent is extended or adjusted under 35 U.S.C. 154(b) by 754 days.

(21) Appl. No.: 09/595,720

(22) Filed: Jun. 16, 2000

Related U.S. Application Data (60) Provisional application No. 60/139,697, filed on Jun. 17, 1999, provisional application No. 60/139,647, filed on Jun. 17, 1999.

(51) Int. Cl.
  *C12Q 1/06* (2006.01)
(52) U.S. Cl. ............... 435/39; 435/6; 435/7.1; 435/287.2; 435/287.9; 435/803; 436/513; 436/161; 210/365; 210/656
(58) Field of Classification Search ............ 435/5, 435/6, 7.92, 7.1–7.2, 7.21, 91.1–91.2, 4, 435/331, 333, 286.5, 287.1, 287.2, 288.4, 435/39, 288.1, 288.6, 803, 287.9; 436/501, 436/518, 512–513, 523–527, 23, 63, 73–74, 436/161, 538–541; 530/412–413; 536/23.1, 536/25.32, 22.1, 24.3; 210/222, 296, 322, 210/635, 656, 767–768, 348; 422/68.1, 59, 422/69–70
See application file for complete search history.

(56) References Cited

U.S. PATENT DOCUMENTS

| | | | | |
|---|---|---|---|---|
| 3,957,436 A | * | 5/1976 | Murray | 436/513 |
| 4,081,246 A | * | 3/1978 | Polito et al. | 436/529 |
| 4,517,303 A | * | 5/1985 | Freytag et al. | 436/501 |
| 4,623,618 A | * | 11/1986 | Rokugawa | 435/6 |
| 4,769,216 A | * | 9/1988 | Chandler et al. | 422/58 |
| 4,943,525 A | * | 7/1990 | Dawson | 435/5 |
| 5,173,293 A | * | 12/1992 | Friend et al. | 424/178.1 |
| 5,246,832 A | * | 9/1993 | Michelson et al. | 435/7.2 |
| 5,273,882 A | * | 12/1993 | Snitman et al. | 435/6 |
| 5,534,407 A | * | 7/1996 | Tabor et al. | 435/5 |
| 5,567,588 A | * | 10/1996 | Gold et al. | 435/6 |
| 5,582,981 A | * | 12/1996 | Toole et al. | 435/6 |
| 5,583,005 A | * | 12/1996 | Nishimura et al. | 435/7.94 |
| 5,646,001 A | * | 7/1997 | Terstappen et al. | 435/7.21 |
| 5,674,727 A | * | 10/1997 | Cole et al. | 435/219 |
| 5,756,291 A | * | 5/1998 | Griffin et al. | 435/6 |
| 5,866,336 A | * | 2/1999 | Nazarenko et al. | 435/6 |

(Continued)

FOREIGN PATENT DOCUMENTS

WO  WO91/19813  12/1991

(Continued)

OTHER PUBLICATIONS

Bieche et al. Novel approach to quantitative polymerase chain reaction using real-time detection: application to the detection of gene amplification in breast cancer. International Journal of Cancer, 78:661-666, 1998.*

(Continued)

*Primary Examiner*—Long V. Le
*Assistant Examiner*—Leon Y. Lum
(74) *Attorney, Agent, or Firm*—Bromberg & Sunstein LLP (57) ABSTRACT

A method for quantitatively assaying one or more target molecules in a sample uses a nucleic acid aptamer that is specific for each target molecule. A quantitative replicative procedure is used to determine a quantity of aptamer specific for each molecule.

36 Claims, 4 Drawing Sheets

U.S. PATENT DOCUMENTS

| | | | | |
|---|---|---|---|---|
| 5,989,823 | A | * 11/1999 | Jayasena et al. | 435/6 |
| 6,054,274 | A | * 4/2000 | Sampson et al. | 435/6 |
| 6,180,348 | B1 | * 1/2001 | Li | 435/6 |
| 6,180,415 | B1 | * 1/2001 | Schultz et al. | 436/518 |
| 6,242,246 | B1 | * 6/2001 | Gold et al. | 435/287.1 |
| 6,281,245 | B1 | * 8/2001 | Patel et al. | 514/575 |
| 6,287,765 | B1 | * 9/2001 | Cubicciotti | 435/6 |
| 2002/0051974 | A1 | * 5/2002 | Dodge et al. | 435/6 |

FOREIGN PATENT DOCUMENTS

| | | |
|---|---|---|
| WO | WO 95/07364 | 3/1995 |
| WO | WO 96/10576 | * 4/1996 |
| WO | WO 99/07724 | 2/1999 |

OTHER PUBLICATIONS

Berndt, C. et al. Quantitative polymerase chain reaction using a DNA hybridization assay based on surface-activated microplates. Analytical Biochemistry, 225:252-257, 1995.*

Gold, Larry. Oligonucleotides as research, diagnostic, and therapeutic agents. The Journal of Biological Chemistry, 270(23):13581-13584, 1995.*

Greenspan, N.S. et al. Idiotypes: structure and immunogenicity. FASEB J, 7:437-444, 1993.*

Huang, S.-C. et al. Binding of biotinylated DNA to streptavidin-coated polystyrene latex: effects of chain length and particle size. Analytical Biochemistry, 237:115-122, 1996.*

Male, D. et al. (1987) Advanced Immunology, Gower Medical Publishing, London, U.K.*

Mandal, S.S. et al. Role of the central metal ion and ligand charge in the DNA binding and modication by metallosalen complexes. Bioconjugate Chemistry, 8:798-812, 1997.*

Drolet et al. An enzyme-linked oligonucleotide assay. Nature Biotechnology (1996), vol. 14, pp. 1021-1025.*

Freytag et al., A highly sensitive affinity-column-mediated immunometric assay, as exmplified by digoxin. Clinical Chemistry (1984), vol. 30, No. 3, pp. 417-420.*

Wang et al. RNA molecules that specifically and stoichiometrically bind aminoglycoside antibiotics with high affinities. Biochemistry (1996), vol. 35, pp. 12338-12346.*

Hirayama et al. "Concentrations of Thrombopoietin in Bone Marrow in Normal Subjects and in Patients with Idiopathic Thrombocytopenic Purpura, Aplastic Anemia and Essential Thrombocythemia Correlate With Its mRNA Expression of Bone Marrow Stromal Cells" *Blood* 92(1): 46-52 (1998).

Desjardin et al. "Comparision of the ABI 7700 System (TaqMan) and Competitive PCR for Quantification of IS6110 DNA in Sputum during Treatment of Tuberculosis" *Journal of Clinical Microbiology* 36(7):1964-1976 (1998).

Gibson, U. et al. "A Novel Method for Real Time Quantitative RT-PCR," *Genome Research* 6:995-1001 (1996).

Piatak et al. "Quantitative Competive Polymerase Chain Reaction for Accurate Quantitation of HIV DNA and RNA Species" *BioTechniques* 14:70-81 (1993).

Kaucner, C., et al "Sensitive and Rapid Detection of Viable *Giardia* Cysts and *Cryptospordium parvum* Oocycsts in Large-Volume Water Samples with Would Fiberglass Cartridge Filters and Reverse Transcription-PCR", *Applied and Environmental Microbiology*, May 1998, pp. 1743-1749.

* cited by examiner

QUANTITATIVE ASSAY FOR LOW ABUNDANCE MOLECULES

RELATED APPLICATIONS

This application gains priority from provisional patent application Ser. No. 60/139,647, filed Jun. 17, 1999 and provisional patent application Ser. No. 60/139,697 filed Jun. 17, 1999, both provisional applications herein incorporated by reference.

TECHNICAL FIELD

Embodiments of the invention relate to quantitative assays for low abundance molecules including antibodies to measure an antibody response in a subject.

BACKGROUND ART

The sensitivity of assays for measuring target molecules in a sample is generally constrained by the threshold of detection provided by the selected method. For example, typical detection systems for proteins employ an antibody specific for that protein immobilized on a solid support matrix. The matrix is typically a nitrocellulose filter, and the detection and quantification is based on antibody-protein binding such that the target protein is retained on the filter and then quantitated (usually by detection of a fluorescent or radioactive moiety present on the immobilized antibody, or incorporated in the target molecule). However, limitations in threshold detection levels exist in the art as it is presently known. For example, an antibody that binds specifically to a known protein can have a $K_D$ for that protein that is in the range of $10^{-9}$ molar concentration. If the protein is present at a concentration below the range of the $K_D$, the antibody is not useful for such detection, since the antibody-antigen complex will not form to an appreciable extent and thus the target protein will not be retained on the solid support matrix. Further, formation of even one or a few antibody-antigen complexes cannot be detected in the presence of an excess of other materials. Techniques such as MALDI-TOF and similar analyses require expensive detection and analytical instrumentation which are not commonly available in a medical environment, and are complicated to operate on a high throughput basis.

Aptamers have been developed to bind specifically to target molecules for purposes of identifying the molecules for disease analysis. PCT application number WO 99-07724, by Nextar Pharmaceuticals, Inc., authored by Heilig and Gold, "Nucleic Acid Ligands for Blood-Brain and Cerebrospinal Fluid-Blood Barriers by Tissue SELEX," published Feb. 18, 1999, discloses use of the SELEX system of obtaining a nucleic acid that has a sequence capable of binding a target protein with high affinity and specificity, in this case for components of cerebrospinal fluid and the blood-brain barrier. The nucleic acid having affinity for a target is known as an "aptamer"; aptamers have been developed for a variety of different types of target materials. See also, for example, PCT application number WO 95/07364, by Nexagen, Inc., authored by Gold et al., "Nucleic Acid Ligands and Improved Methods for Producing the Same," published Mar. 16, 1995; and PCT application number WO 91/19813, by University of Colorado Foundation, authored by Gold and Tuerk, "Nucleic Acid Ligands," published Dec. 26, 1991. The foregoing publications and the references cited therein are hereby incorporated herein by reference.

These methods typically use proteins and other molecules as the starting point, and then seek to identify, select, and enrich aptamers capable of binding the target molecules. Of particular interest to those using such methods is the identification of nucleic acid aptamers capable of binding molecules not previously known to bind nucleic acids.

Quantification of nucleic molecules has been achieved using Quantitative Polymerase Chain Reaction (QPCR), Quantitative Competitive Reverse Transcription-PCR [QC (RT)-PCR] or Real Time Detection 5'-Nuclease-PCR (RTDN-PCR; also known as TaqMan RT-PCR), is limited because of its focus on detection of nucleic acids. These techniques have been used to detect and measure concentrations of viable *Cryptosporidium parvum* oocytes present in environmental water concentrates, based on detection of DNA generated with RT-PCR from mRNA obtained from oocytes using oligo(T)$_{25}$ magnetic beads ("Sensitive and Rapid Detection of Viable *Giardia* Cysts and *Cryptosporidium parvum* Oocytes in Large-Volume Water Samples with Wound Fiberglass Cartridge Filters and Reverse Transcription-PCR," C. Kauener and T. Stinear, *Appl. Environ. Microbiol.*, 1998, 64(5): 1743–1756). However, detection is limited by the necessity of obtaining mRNA, an inherently unstable and short-lived species ($t_{1/2}$ values in cells are typically less then 3 minutes for any given mRNA.)

It is also known in the art to correlate the concentration of a protein in a sample tissue to its mRNA expression, such as thrombopoietin in bone marrow cells, by use of TaqMan real-time quantitative RT-PCR ("Concentrations of Thrombopoietin in Bone Marrow in Normal Subjects and in Patients with Idiopathic Thrombocytopenic Purpura, Aplastic Anemia, and Essential Thrombocythemia Correlate With Its mRNA Expression of Bone Marrow Stromal Cells," Y. Hirayama et al., *Blood*, 1998, 92(1): 46–52). This quantitative replicative method relies on the presence of a 5'-nuclease assay in the RT-PCR reactions, wherein a probe (the TaqMan probe) specific for an aptamer directed to the target protein, contains a fluorescent moiety such as 6-carboxyfluorescein (FAM) on the 5'-end, and a phosphate-capped quencher fluor moiety such as 6-carboxytetramethylfluorescein (TAMRA) on the 3'-end of the probe. As amplification of the mRNA for the target protein proceeds, the intensity of fluorescence of the FAM moiety increases as a function of time and mRNA concentration due to 5'-endonuclease cleavage of the probe, releasing more and more FAM moiety into the solution.

Again, this method is limited by the requirement for mRNA, and also is limited in that the concentration of thrombopoietin calculated in the sample is only a correlation to mRNA expression, it is not a measurement of thrombopoietin itself, or a measurement of a molecule which can be related directly to target protein concentration.

In other prior art, it is known to use either TaqMan RT-PCR coupled with an ABI Prism 7700 Sequence Detection System, or Competitive PCR for quantification of DNA from a bacterial pathogen in the sputum of patients during treatment (see "Comparison of the ABI 7700 System (TaqMan) and Competitive PCR for Quantification of IS6110 DNA in Sputum During Treatment of Tuberculosis," Desjardin, L.e. et al., *J. Clin. Microbiol.* 1998, 36(7): 1964–1976). The two methods were found to be reproducible and accurate, and comparable in terms of detection limits. However, both methods were limited by poor correlation between quantity of *M. tuberculosis* DNA determined and the number of cultivable bacilli in the sputum specimen.

Quantitative replicative methods are thus focused on measurement of nucleic acids or its expression to determine protein concentration. Methods such as SELEX for generation, selection, and enrichment of nucleic acid aptamers are focused on the aptamer itself, e.g. finding aptamers which bind to unusual target molecules not previously known to bind nucleic acids, or finding aptamers which distinguish molecules of close chemical make-up, such as aptamers which can distinguish caffeine and theophyllin—molecules in the purine family which differ only in the presence or absence of a methyl group. In other methods, the nucleic acid aptamers are designed to prevent antibody interaction with its target receptor cell, in efforts to inhibit the allergic response (see for example, PCT application number WO 96/10576, by Nextar Pharmaceuticals, Inc. authored by Wiegand et al., "High Affinity Oligonucleotide Ligands to Immunoglobulin E (IgE)" published Apr. 11, 1996).

SUMMARY

Embodiments of the invention relate to the detection of low abundance molecules using a novel approach that relies on aptamers to bind the target molecule and determining the concentration of low abundance molecules based on the concentration of aptamers.

A specific embodiment of the invention includes a method for quantitatively assaying one or more target molecules in a first sample that includes: adding to the first sample, a preparation of a nucleic acid aptamer specific for each target molecule; allowing substantially all of the target molecules in the first sample to bind with the aptamers; separating unbound aptamers from the first sample by contacting the sample with immobilized ligands wherein the ligands bind to the unbound aptamers; recovering a second sample containing the aptamer bound to target molecules; and using a quantitative replicative procedure to determine a quantity related to the concentration of the aptamer in the second sample and therefore related to the concentration of target molecules in the first sample.

In preferred embodiments, the nucleic acid aptamer is selected from the group consisting of natural or synthetic single-stranded DNA, double-stranded DNA, single-stranded RNA, double-stranded RNA and chemical modifications thereof. The target molecules may be present in the sample at molar concentrations less than their dissociation constants with respect to the aptamers and may be low abundance molecules. The target molecules may include biological macromolecules which may be selected from the group consisting of a protein, a lipid, a polysaccharide or combinations thereof. The target molecules may include small organic molecules and furthermore may be selected from a group consisting of antibiotics, vitamins, steroids, and pesticides. The target molecules may include inorganic molecules, more particularly metals, more particularly metal ions, metal oxides, and metal complexes. The target molecules may also be an antibody, more particularly IgE, more particularly a plurality of antibody molecules belonging to different subclasses characterized by a difference in the hypervariable region of the antibody, more particularly a subclass of an antibody having a characteristic hypervariable region. In a preferred embodiment, the aptamer binds to a constant region of the antibody.

In a preferred embodiment, the first sample is obtained from an animal subject, more particularly organ tissue, muscle tissue, bone tissue, connective tissue, fetal, placental, lymphatic tissue, vascular tissue, neuronal tissue. The sample may be a biological fluid selected from blood, lymph, urine, sputum, joint including spinal fluid, and saliva. The first sample may be an environmental sample, including samples obtained from a plant, water, food beverages including milk, and industrial waste.

In a preferred embodiment, the immobilized ligand is immobilized on a support matrix selected from the group consisting of resins, beads, including magnetic beads, gels, cellulose and silica. More particularly, the immobilized ligand is immobilized on an affinity column. The immobilized ligand may be the constant region of the antibody for removing unbound aptamer from the sample.

In a preferred embodiment, the quantitative replicative procedure is a quantitative polymerase chain reaction. The method may further include measuring the amount of aptamer bound to the target molecule further including denaturing the aptamer so as to separate the nucleic acid from the target molecules. In further embodiments, oligonucleotide primers are added to the sample after denaturing the aptamer from the target molecules.

In a preferred embodiment, a method is provided as described above in which the target molecules are antibodies and the second sample contains antibody-bound aptamer, the second sample being divided into a plurality of aliquots, a first aliquot of the second sample being assayed using a quantitative replicative technique to determine an amount of antibody in the first sample. Moreover, the method may further include the steps of contacting a second aliquot of the second sample with an immobilized ligand for binding an antibody with a first hypervariable region; wherein the antibody with a first hypervariable region is one of the target molecules in the first sample; recovering a third sample containing the aptamer bound to target molecules excluding the antibody with the first hypervariable region; assaying the aptamer concentration in the third sample using the quantitative replicative technique, so as to determine a difference in an amount of aptamer in the second sample and the third sample; and obtaining a measure of an amount of the antibody with the first hypervariable region in the first sample from the difference. Alternatively, the method may include the steps of: (a) contacting a plurality of aliquots of the second sample with an immobilized ligand wherein the ligand is immobilized by attachment to a substrate in a single chamber, or to multiple substrates wherein each substrate is contained in a separate chamber, each immobilized ligand having a specificity for an antibody with a different hypervariable site; (b) recovering a third sample containing the aptamer bound to target molecules excluding the antibody bound to immobilized ligand; (c) assaying the aptamer concentration in the third sample using the quantitative replicative technique, so as to determine a difference in an amount of aptamer in the second sample and the third sample; and (d) obtaining a measure of the antibody with the hypervariable region in the first sample from the difference.

In a specific embodiment, a method is provided that includes: quantitatively evaluating in vitro an antibody response of a subject to an antigen, the method including obtaining a sample from the subject and an aptamer for binding generally to all antibodies of a common class; allowing substantially all of such antibodies in the sample to bind the aptamer in a common class mixture, so that the common class mixture includes antibody-aptamer complexes; using antigen-antibody affinity binding to separate from an aliquot of the common class mixture those of the antibody-aptamer complexes having antibodies specific to the antigen, to produce (I) an antigen-specific antibody-aptamer complex and (ii) a difference mixture; and, using a quantitative replicative procedure to determine a quantity related to the concentration of the antigen-specific antibody-aptamer complex relative to the concentration of the antibody-aptamer complexes in the common class mixture, and therefore related to the response of the subject to the antigen.

In a specific embodiment of the invention, a method is provided for quantitatively evaluating in vitro the response of a subject to a plurality of different antigens, the method that includes: obtaining a sample from the subject and adding an aptamer for binding generally to all antibodies of a common class in the tissue; allowing substantially all of such antibodies in the sample to form a complex with the aptamer in a common class mixture, so that the common class mixture includes antibody-aptamer complexes; using antigen-antibody affinity binding to separate, from each of a plurality of aliquots of the common class mixture, those of the antibody-aptamer complexes having antibodies specific to a different one of the antigens, to produce with respect to each different antigen (i) an antigen-specific antibody-aptamer complex and (ii) a difference mixture; and, using a quantitative replicative procedure to determine a quantity related to the concentration of each different antigen-specific antibody-aptamer complex relative to the concentration of the antibody-aptamer complexes in the common class mixture, and therefore related to the response of the subject's tissue to each of the different antigens.

In a preferred embodiment, a kit is provided for determining the allergic response of a subject to an allergen, that includes: an aptamer specific for a common class of IgE and a plurality of aptamers specific for individual allergens; a plurality of reaction chambers for holding individual aliquots of a sample taken from the subject after binding the common class of antibody and removing unbound aptamer; an immobilized antibody for binding unbound aptamer of the common class prior to dividing the sample into aliquots, and allergen for binding specific antibodies; and, means for quantitatively replicating the aptamers of the common class of IgE and for the aptamer-IgE complexes not bound to the allergen.

BRIEF DESCRIPTION OF THE DRAWINGS

The foregoing features of the invention will be more readily understood by reference to the following detailed description, taken with reference to the accompanying drawings, in which.

DETAILED DESCRIPTION OF EMBODIMENTS OF THE INVENTION

Embodiments of the invention allow the amount of target molecules in multiple samples to be determined using quantitative replicative techniques to measure the amount of aptamer bound to the target molecule and hence to determine the amount of target molecule. Novel features of the methods described herein include the use of a single entity that is both the binding entity and the reporter molecule. Moreover, the binding entity has the advantageous feature of having a "tight" binding constant of the order of $10^{-11}$ to $10^{-12}$ molar.

Quantification of target molecules present in very low abundance in the sample may be determined down to a theoretical single target molecule because the method does not require the target molecule be present in the sample at concentrations greater than the $K_D$ value of the target molecule for its specific aptamer. Thus, the methods provided herein can be used to detect low abundance molecules in the environment or in a subject or elsewhere.

To illustrate the utility of embodiments of the invention, the method may be used to diagnose the presence of a protein product of a cell or a tissue at an earlier stage of development, that might be indicative of a pathological condition such as a tumor or an infection. For example, a small number of molecules indicative of malformation of the fetus such as α-fetoprotein, indicative of defects in the central nervous, system may be detected.

Alternatively, tumor markers such as nestin, indicative of metastasis of a melanoma, can be detected using the methods described herein. The methods may also be applied to improved and earlier detection of prostatic serum antigen (PSA), a marker for prostate cancer and a marker for recurrence of the cancer post-surgery.

Alternatively, the methods described herein may be used to measure the concentration of a common class target molecule in a sample, such as the IgE class antibodies which are produced in allergic reactions, and further, may be used for the quantification of specific molecules within the common class, such as $IgE_1$, $IgE_2$, $IgE_3$ ... $IgE_x$. The advantages of combining the use of specific aptamers directed to a common class of target molecules, or to specific molecules within the common class, with quantitative replicative procedures include the ability to determine the amount of aptamer bound to target molecule in the sample, and thus a quantity of target molecule present in the sample. This approach allows quick, accurate and relatively non-invasive analysis of for example, IgE, for analyzing an allergic reaction, wherein a single blood sample may be used for analysis, rather than 20 or more skin pricks whose results are often ambiguous and merely qualitative at best.

Similarly, exposure of a person to a pathogen triggers an IgG antibody response, such that class IgG antibodies are generated against the specific pathogen. The number and quantity of IgG antibodies present in a person is indicative of prior exposure and potential immunity upon re-exposure to that same pathogen. For example, whereas antibody detection of an infectious organism such as *Mycobacterium tuberculosis*, or a virus such as rubella or smallpox, relies on withdrawing a sample of blood from the person, performing serial dilutions and assaying each dilution individually according to the prior art, the methods described here may be used to quantify antibody titer in a subject in a single reaction.

Additional examples of embodiments of the invention include environmental analysis such as measuring the quantity of growth hormones present in milk; determination of the quantity of pathogenic bacteria such as *E. coli* O1157:H7 in meat or drinking water; or determination of the quantity of a class of antibodies, such as IgE or IgG, in a blood or tissue sample; or the quantity of a specific IgE or IgG antibody in a blood or tissue sample. Thus, the method can be used to determine I) allergic response to various antigens, or ii) an immunity profile of a patient to show which pathogens they have been exposed to, or iii) contamination of pathogenic organisms in food or drinking supplies, or iv) contamination of food or drinking supplies from pesticides or agricultural livestock food supplements.

Embodiments of the invention provide a method for quantification of target molecules from any of a variety of samples, which does not rely on radioactive reagents, can be detected independent of concentration, and is versatile, fast, and accurate.

The following terms as used here and in the claims are defined as follows:

"Quantitatively assaying a target molecule" means a method which determines a quantity of nucleic acid aptamer using a replicative polymerase reaction, and then relates that quantity of aptamer to a quantity of target molecule.

"Target molecule" includes any macromolecule, including protein, carbohydrate, polysaccharide, glycoprotein, receptor, antigen, antibody, growth factor; or it may be any small organic molecule including a hormone, substrate, metabolite, cofactor, inhibitor, drug, dye, nutrient, pesticide, peptide; or it may be an inorganic molecule including a metal, metal ion, metal oxide, and metal complex; it may also be an entire organism including a bacterium, virus, and single-cell eukaryote such as a protozoon.

"Aptamer" means a natural or non-natural nucleic acid molecule with affinity for a target molecule.

"Natural nucleic acids" means those derived from natural sequences or sources.

"Synthetic nucleic acids" means those derived from non-natural sequences, which may contain modified nucleotides, prepared using either chemical or enzymatic synthesis, restriction endonucleases, recombinant techniques, or otherwise.

"Immobilized ligands" mean target molecules, or aptamer-binding regions of target molecules, that have been covalently or non-dissociably bound to a support matrix.

"Support matrix" means any resin, bead, including magnetic bead, gel, cellulose, including nitrocellulose filter, silica, alumina, or other solid material.

"Affinity column" means a column for separation of molecules, wherein the separation is achieved because of covalently or non-dissociably bound molecules selecting for a target molecule.

"A sample obtained from an animal subject" may be a tissue sample, including organ, muscle, bone, connective, fetal, placental, lymphatic, vascular, and neuronal tissue; or it may be a biological fluid sample selected from blood, lymph, urine, sputum, joint, spinal and saliva fluid.

"Environmental sample" in the context of this application means non-animal sample, including plant tissue, water, beverages including milk, and industrial waste.

"Hypervariable" means a region of a molecule, most commonly an antibody, subject to inherent instability of sequence, such that mutation occurs frequently in response to exogenous pressures (for example—exposure to a foreign substance, commonly referred to as an antigen—to produce new sequences). "Constant region" means that region of a molecule, most commonly an antibody, that is inherently stable with respect to mutation pressures.

"Exogenous antigen" means any antigen, including allergens, not produced or native to the sample being assayed, for example dust mites, pollen, mold, bee venom, poison ivy extract, and others of such type.

"Region" as used herein is a reaction vessel including 1-mL and 500-µL Eppendorf tubes, test tubes, and wells in multi-well plates.

Embodiments of the invention relate to a method and kit for quantitatively assaying one or more target molecules in a sample through use of a nucleic acid aptamer specific for the target molecule. The aptamers are DNA or RNA nucleic acid sequences in the range of 15–100 nucleotides, and are prepared by chemical or enzymatic synthesis, or by restriction endonuclease treatment or recombinant technology, and may be modified. Using amplification and enrichment techniques, the aptamers can be selected for binding affinity to any of a number of target molecules.

Upon mixing the aptamer with a sample containing target molecule, the aptamer binds to the target molecule and the aptamer-bound target molecule is then separated from the remaining mixture by the use of affinity. Specifically, immobilized ligands, which may be target molecule or portions of the target molecule which bind the specific aptamer, are utilized to remove any unbound aptamer from the mixture, leaving only aptamer-bound target molecule in the remaining sample mixture. Then, by use of a quantitative replicative procedure, the quantity of aptamer bound to the target molecule is determined, which therefore relates to the quantity of target molecule present in the original sample.

The target molecules may be whole organisms such as bacterium, virus, or single-celled protozoan pathogens; they may be biological macromolecules such as proteins, lipids and carbohydrates; or they may be organic or inorganic molecules such as pesticides, vitamins, and metals. The target molecules may be present in samples of animal tissue, biological fluid, or environmental substances such as plant material, water, beverages, and industrial waste. The immobilized ligands employed in the affinity separation may be attached to a solid support matrix covalently or non-dissociably, and the support matrix may be any material in the art used for such purposes.

The quantitative replicative procedure may involve standard PCR or RT-PCR techniques, in combination with a 5'-nuclease assay involving addition of a fluorogenic probe specific for the aptamer being amplified by PCR or RT-PCR, or in combination with molecular energy transfer (MET) or fluorescence resonance energy transfer (FRET) moieties present on the primers used for amplification. When 5'-nuclease assay is also used, upon binding to the aptamer, the probe, typically labeled with a fluorescent moiety on the 5'-end and a phosphate-capped fluorescent-quenching dye on its 3'-end, is degraded by the 5'-nuclease. As each terminal 5'-nucleotide is released by the nuclease activity, fluorescence occurs and increases with time and amplification of the aptamer. Thus, a real-time measurement of fluorescence increase can be plotted, allowing quantification of aptamer bound to target molecule, which is directly related to quantity of target molecule.

When FRET moieties are used, the primers contain fluorescent donor and acceptor moieties, such that the fluorescence is quenched until primer incorporation into the amplified aptamer product, whereupon quenching stops (because of a conformation change in the primer, for example) and fluorescence is detected. This method has the advantage of allowing direct quantitation of aptamer amplification. (U.S. Pat. No. 5,866,336 entitled "Nucleic Acid Amplification of Oligonucleotides with Molecular Energy Transfer Labels and Methods Based Thereon," Nazarenko, I. A. et al., issued Feb. 2, 1999).

Embodiments of the invention also relate to methods for quantitatively assaying for low abundance target molecules, present at either molar concentrations less than the dissociation constants for their respective specific aptamers, or present in the sample at nanomolar levels or below. The quantitative replicative procedure utilized in embodiments of the invention is capable of amplifying a single nucleic acid aptamer, in theory, and thus is not limited to concentration requirements of other detection methods of the prior art.

In a preferred embodiment, the aptamer is specific for a low abundance target molecule, for example the tumor marker nestin, indicative of a metastatic melanoma. Accordingly, the sample may be human tissue from a biopsy, and the aptamer specific for a region on the nestin tumor marker. The sample tissue and aptamer are mixed together, and all nestin in the sample then binds to the specific aptamer. The sample mixture is then applied to an affinity column or to nitrocellulose filters containing immobilized nestin tumor marker. This step removes all unbound aptamer from the sample mix, leaving only aptamer-bound tumor marker in the solution. Then, quantitative replicative methodology is employed to amplify and quantitate the amount of aptamer bound to the tumor marker. This quantity is then used to determine a quantity of tumor marker originally present in the biopsied tissue sample.

In a second preferred embodiment, the aptamer is specific for a small organic target molecule, exemplified by a pesticide such as one in the synthetic estrogen family. The sample may be an environmental sample such as ground water or plant extract. The aptamer is added to the sample, whereupon all target molecule binds to the aptamer. The remaining unbound aptamer is separated from the sample mixture by application of the mixture to an affinity column containing immobilized pesticide. The eluate from the column then contains only aptamer-bound pesticide. Quantitative replicative procedures are then performed on the eluate, and a quantity determined for the aptamer bound to the pesticide target molecule, which is then used to determine a quantity of pesticide present in the original sample.

In another preferred embodiment, the aptamer is specific for a common region in target molecules of a general common class, exemplified by the class of IgE antibodies. The common class further includes a plurality of specific target molecules within that common class, for example antigen-specific $IgE_x$ antibodies within the class IgE antibodies. The sample may be human blood, and the aptamer specific for the $F_C$ constant region of the IgE antibody class. Upon mixing, all IgE molecules bind to the aptamer, and unbound aptamer is removed by application of the sample mixture to an affinity column containing the $F_C$ constant region of IgE immobilized to the solid support matrix. Thereupon, the eluate from the affinity column, containing only aptamer-bound common class target molecule, is divided into aliquots, and individual aliquots are applied to a second set of separate affinity columns containing immobilized antigen or aptamer specific for the $F_{AB}$ hypervariable region of a number of specific $IgE_x$ antibodies. A quantitative replicative procedure, such as Quantitative Polymerase Chain Reaction (QPCR), coupled with 5'-nuclease assay and fluorescently labeled probes, or FRET methodology and fluorescent donor/acceptor pairs, is then performed on the eluate from the second column and on an aliquot of eluate from the first column. The difference in values determined for quantity of aptamer bound to IgE from each column eluate is therefore the quantity for each of the specific $IgE_x$ antibodies present in the sample.

For ease of understanding, specific sections of the preferred embodiments are now discussed as separate headings.

A. Preparation of Nucleic Acid Aptamers Specific for a Target Molecule

One method for preparation of nucleic acid aptamers specific for a desired target molecule involves the use of successive repetitive cycles of the following steps: I) production of random aptamer sequences; ii) binding of aptamers to a desired target molecule; and iii) partitioning, dissociation, and amplification of aptamers which bind to desired target molecule, thus generating an enriched sample of high-affinity aptamers for the desired target molecule. See e.g. PCT application number WO 91/19813, "Nucleic Acid Ligands" by University of Colorado Foundation, authored by Gold and Tuerk, published Dec. 26, 1991; PCT application number WO 95/07364, "Nucleic Acid Ligands and Improved Methods for Producing the Same" by Nexagen, Inc., authored by Gold et. al., published Mar. 16, 1995; PCT application number WO 99/07724, "Nucleic Acid Ligands for Blood-Brain and Cerebrospinal Fluid-Blood Barriers by Tissue SELEX" by Nextar Pharmaceuticals, Inc., authored by Heilig and Gold, published Feb. 18, 1999.

The nucleic acid sequence itself may be single-stranded DNA or RNA, double-stranded DNA or RNA, derive from natural sources and sequences, or be synthesized by chemical or enzymatic methodology from natural or non-natural sequences, and may also contain modified nucleotides.

The aptamer used to detect target molecules is both the binding molecule and the reporter entity. This dual role permits quantification of the target molecule by quantifying the aptamer that binds to the target. Moreover, the aptamers have $K_D$ values for their target molecules of $10^{-11}$ to greater than $10^{-12}$ molar. Aptamers with such tight binding affinities for their respective target molecules allow quantification of target molecules in samples present at extremely low concentrations.

One preferred embodiment allows quantification of target molecules present in the sample at molar concentrations less than the $K_D$ values for their respective aptamers. Because the aptamers bind their target molecules so tightly, and because the replicative quantitative methods are so sensitive, in theory the aptamer molecule from a single aptamer-target molecule complex can be replicated, amplified and quantitated, thus providing quantification of target molecule present in solution, even at extremely low concentrations.

Another preferred embodiment allows quantification of target molecules present in a sample at molar concentrations greater than or equal to the $K_D$ values for their respective aptamers. Again, the aptamers bind their target molecules very tightly. The presence of excess aptamer permits essentially all target molecules to bind the aptamer. Quantification of the aptamer bound to all target molecules thus provides a reliable quantification of total target molecule originally present in the sample.

B. Target Molecules and Sample

Target molecules, including macromolecules, small organic molecules, inorganic molecules, or whole organisms will be present in a variety of samples to analyze. These samples may be obtained by standard methods known in the art. For example, tissue samples from animals may be obtained by biopsy or simply by removing a slice from an excised organ or deceased specimen, and may be further prepared with homogenization, filtration, precipitation, or the like; plant tissues may be also require homogenization or extraction treatments. Biological fluid may be obtained by syringe or lancing, and may then be further filtered, centrifuged, or diluted as needed. Similarly, environmental samples may be collected from water sources, industrial waste fluids, and beverages and may require additional treatment as above.

C. Immobilized Ligands

Immobilized ligands includes target molecules, or aptamer-binding regions of target molecules, that have been covalently or non-dissociably bound to a support matrix using technology common to one skilled in the art. Peptides and proteins are routinely covalently linked at the terminal amine to a solid support matrix including agarose, silica, and cellulose. Many pre-linked materials are even available commercially, for example, agarose-bound concavalin A, specific for thrombin (Vector Laboratories, cat. No. AL-1003). This covalently linked material allows preparation of an agarose affinity column having an immobilized thrombin ligand, wherein the covalently-linked concavalin A on the agarose binds thrombin specifically and non-dissociably, thereby allowing subsequent affinity separation of any molecule which is specific for thrombin.

D. Real Time Quantitative Replicative Techniques

Quantitative Replicative Techniques are those which permit real time quantification of a desired target molecule or molecules present in a sample, by comparison to quantification of a nucleic acid aptamer sequence present in the sample vessel and bound specifically to the target molecule. First, the aptamer is replicatively amplified using standard PCR or RT-PCR techniques, such that an amount of amplified aptamer may be quantitated by relationship to the number of replicative cycles required for its detection. The number of cycles required for sufficient replication of the aptamer molecule is related to its low level of abundance. Thus for example if 12 cycles of replication are required to synthesize sufficient copies for detection, the protein is in greater abundance than if 20 or 25 cycles of replication are required. Then, that quantity of aptamer is used to determine the quantity of desired target molecule present in the sample, to which the aptamer was specifically bound in a one to one ratio before amplification.

Various embodiments of the invention utilize a DNA aptamer and one of a set of well-characterized DNA polymerases, for example, a heat stable polymerase such as Taq polymerase isolated from the bacterium *Thermus aquaticus*, or a polymerase which is a Pfu polymerase isolated from the bacterium *Pyrococcus furioso*. Both enzymes are available from New England Biolabs, Beverly, Mass. Cycles of replicative synthesis can also be obtained with conventional non-heat stable enzymes, by addition of enzyme following each heating step to denature the nucleic acid product, in a series of alternating heating and low temperature synthesis steps. It is necessary in these replicative reactions that primers complementary to each of the 5' and 3' ends of the aptamer nucleic acid be included in the reaction mix, such that synthesis proceeds using the primers for extension to copy the aptamer template, in sufficient quantity that cycles of replication are not limited by the absence of primers. In an embodiment of the invention, the replicative steps are performed using quantitative polymerase chain reaction as described in references infra.

Polymerase reactions typically include all the substrates necessary to replicate the nucleic acid, for example DNA substrates require dATP, dCTP, dTTP, and dGTP, at concentrations sufficient to remain above the $K_M$ of the enzyme throughout a sufficient number of cycles to distinguish the abundances of each of a plurality of proteins being assayed. These concentrations are familiar to one of ordinary skill in the art of synthesis of nucleic acids.

During amplification of the aptamer using standard PCR methods, one method for detection and quantification of amplified aptamer results from the presence of a fluorogenic probe. The probe, which is specific for the aptamer, typically has a 6-carboxyfluorescein (FAM) moiety covalently bound to the 5'-end and a 6-carboxytetramethylrhodamine (TAMRA) or other fluorescent-quenching dye (easily prepared using standard automated DNA synthesis) present on the 3'-end, along with a 3'-phosphate to prevent elongation. The probe is added with 5'-nuclease to the PCR assays, such that 5'-nuclease cleavage of the probe∘aptamer duplex results in release of the 5'-bound FAM moiety from the oligonucleotide probe. As amplification continues and more aptamer is replicated by the PCR or RT-PCR enzymes, more FAM is released per cycle and so intensity of fluorescence signal per cycle increases. The relative increase in FAM emission is monitored during PCR or RT-PCR amplification using an analytical thermal cycler, or a combined thermal cycler/laser/detector/software system such as an ABI 7700 Sequence Detector (Applied Biosystems, Foster City, Calif.). The ABI instrument has the advantage of allowing analysis and display of quantification in less than 60 s upon termination of the amplification reactions. Both detection systems employ an internal control or standard wherein a second aptamer sequence utilizing the same primers for amplification but having a different sequence and thus different probe, is amplified, monitored and quantitated simultaneously as that for the desired target molecule (see "A Novel Method for Real Time Quantitative RT-PCR," Gibson, U. et. al., 1996, *Genome Res.* 6:995–1001; Piatak, M. et. al., 1993, *BioTechniques* 14:70–81; "Comparison of the BI 7700 System (TaqMan) and Competitive PCR for Quantification of IS6110 DNA in Sputum During Treatment of Tuberculosis," Desjardin, L.e. et. al., 1998, *J. Clin. Microbiol.* 36(7):1964–1976).

In another method for detection and quantification of aptamer during amplification, the primers used for amplification contain molecular energy transfer (MET) moieties, specifically fluorescent resonance energy transfer (FRET) moieties, whereby the primers contain both a donor and an acceptor molecule. The FRET pair typically contains a fluorophore donor moiety such as 5-carboxyfluorescein (FAM) or 6-carboxy-4,5-dichloro-2,7-dimethoxyfluorescein (JOE), with an emission maximum of 525 or 546 nm, respectively, paired with an acceptor moiety such as N'N'N'N'-tetramethyl-6-carboxyrhodamine (TAMRA), 6-carboxy-X-rhodamine (ROX) or 6-carboxyrhodamine (R6G), all of which have excitation maximum of 514 nm. The primer may be a hairpin such that the 5'-end of the primer contains the FRET donor, and the 3'-end (based-paired to the 5'-end to form the stem region of the hairpin) contains the FRET acceptor, or quencher. The two moieties in the FRET pair are separated by approximately 15–25 nucleotides in length when the hairpin primer is linearized. While the primer is in the hairpin conformation, no fluorescence is detected. Thus, fluorescence by the donor is only detected when the primer is in a linearized conformation, i.e. when it is incorporated into a double-stranded amplification product. Such a method allows direct quantification of the amount of aptamer bound to target molecule in the sample mixture, and this quantity is then used to determine the amount of target molecule originally present in the sample (see U.S. Pat. No. 5,866,336, "Nucleic Acid Amplification of Oligonucleotides with Molecular Energy Transfer Labels and Methods Based Thereon," Nazarenko, I. A. et al., issued Feb. 2, 1999).

E. Antibody Structure

Antibody molecules generally have two light chains—the L chains—each having about 100 amino acids residues, and two heavy chains—the H chains—each having about 150 amino acid residues, the four chains connected by intramolecular disulfide bonds to form the intact antibody of type $H_2L_2$, having a molecular weight of about 500 kDa. In the prototypical "Y"-shaped drawing of the molecule, the inner arms of the Y are comprised of the entire light chains, and are connected by intramolecular disulfide bonds to the amino-termini of the heavy chains. The stem of the Y contains the carboxy-termini of the heavy chains. When cleaved by an endopeptidase, the inner arms of the antibody, which have the antigen binding determinant known as the hypervariable or $F_{AB}$ region, can be separated from the stem which contains the constant $F_C$ (crystalline) region and the determinant that enables the antibody molecule to bind to an antibody receptor on a cell. Because all antibody molecules of a given class, e.g., IgE, have a common $F_C$ region, they can be obtained by separation on this basis, using affinity chromatography for example, whereby an IgE $F_C$-specific aptamer is immobilized on a solid support matrix and the IgE antibody-containing sample is applied to the column.

Two different sizes of antibody molecules, IgM and IgG, were originally identified by analysis of the size of the proteins. IgM is a pentamer of the $H_2L_2$ protein molecule, in which each monomer is covalently bonded by disulfide bridges at the $F_C$ end. IgG, and other subsequently identified antibody common classes, including IgE, are monomers of the $H_2L_2$ structure. IgE level is substantially elevated in subjects having allergies; for example, total IgE blood content can be two, three, or even four orders of magnitude higher in an allergic subject than in a normal subject. In a subject having one or multiple allergies, the excess IgE molecules are populations of polyclonal antibodies, each population having larger than normal quantities, and each population comprising antigen-binding determinants in the $F_{AB}$ for that class of antigens to which the person is sensitive.

Similarly, the IgG fraction from a subject reflecting recent and long-term exposure to antigens throughout the life of the subject is a set of polyclonal populations. Thus a person having been exposed to rubella several decades earlier will retain a very small number of circulating IgG molecules having $F_{AB}$ antigenic determinants specific for a rubella antigen. Recent re-exposure to rubella would enable that person to expand the number of clones of B cells and the number of each clone capable of synthesizing the IgG molecules that can bind the $F_{AB}$ sites to the antigens on the virus. Thus, the diversity of the circulating IgG population reflects the capability of producing a repertoire of immune responses upon re-exposure to an antigen, and the amount of any one species of circulating IgG molecule can indicate how recently a subject has been exposed or re-exposed. Similarly, the amount of any one of a population of antigen specific circulating IgE molecules indicates the extent of allergic response of the subject to the cognate antigen or antigens used in the method.

F. Quantification of Low Abundance Target Molecules

One preferred embodiment allows detection and quantification of low abundance molecules present in a sample. An aptamer specific for the desired target molecule is allowed to combine with the target molecule in a sample, such that all the target molecule binds to the aptamer. Thereon the excess unbound aptamer is separated from the target molecule-bound aptamer using affinity of that aptamer for the target molecule, for example employing an affinity column wherein the target molecule, or the portion of it which binds to the aptamer, is covalently or non-dissociably bound to the support matrix of the column. After applying the sample/aptamer solution to the affinity column, all unbound aptamer will bind to the column, leaving only target molecule-aptamer complexes in the eluate. Upon replicative amplification of the denatured aptamer from the bound complexes, combined with the 5'-nuclease PCR assay, a real time quantification of the aptamer bound to the target molecule can be determined. The quantification of aptamer is based on the number of replicative cycles required for detection as compared to an internal standard, and the quantity of aptamer is then used to determine quantity of target molecule present in the original sample.

Figure 1:
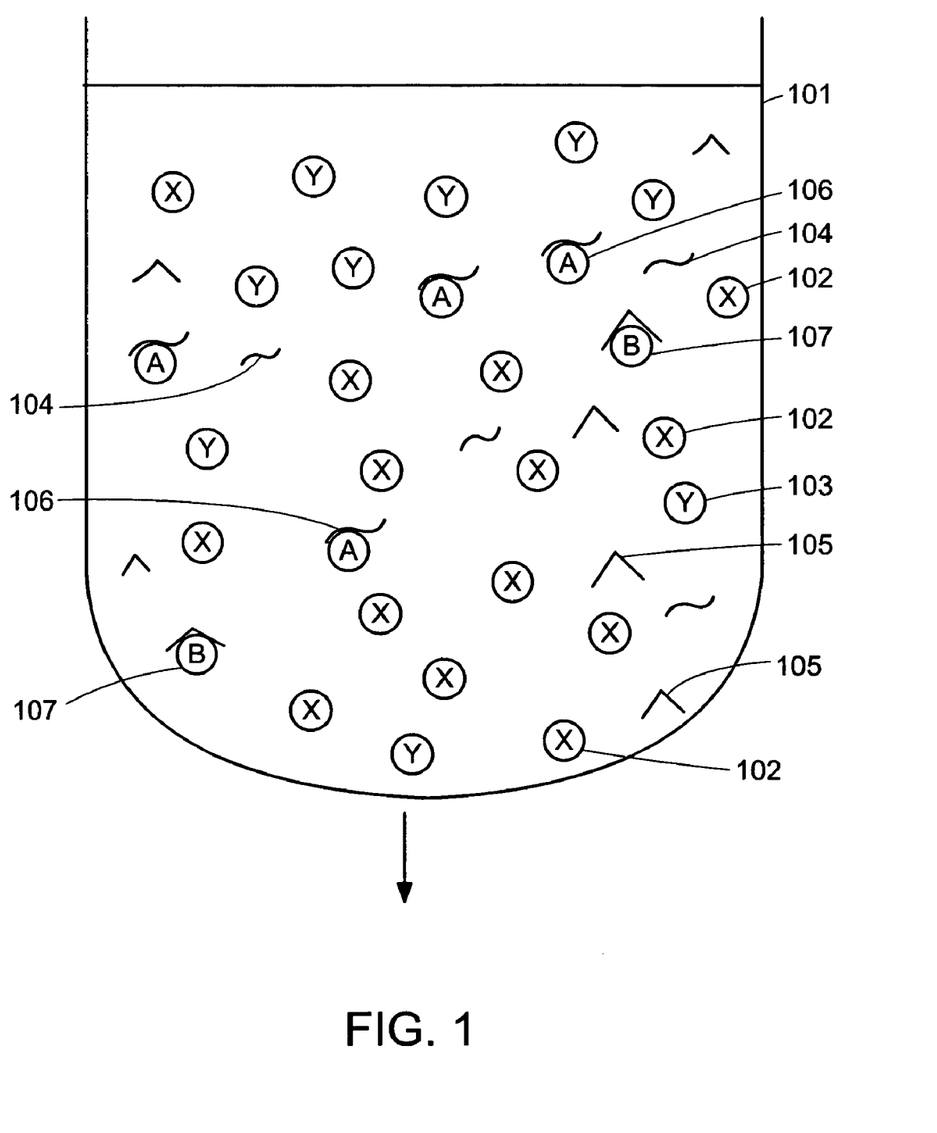
FIG. 1 illustrates schematically an intermediate stage after addition of aptamers to a sample in a reaction vessel to determine the presence of low abundance molecules by allowing aptamer to bind target molecules.
Figure 2:
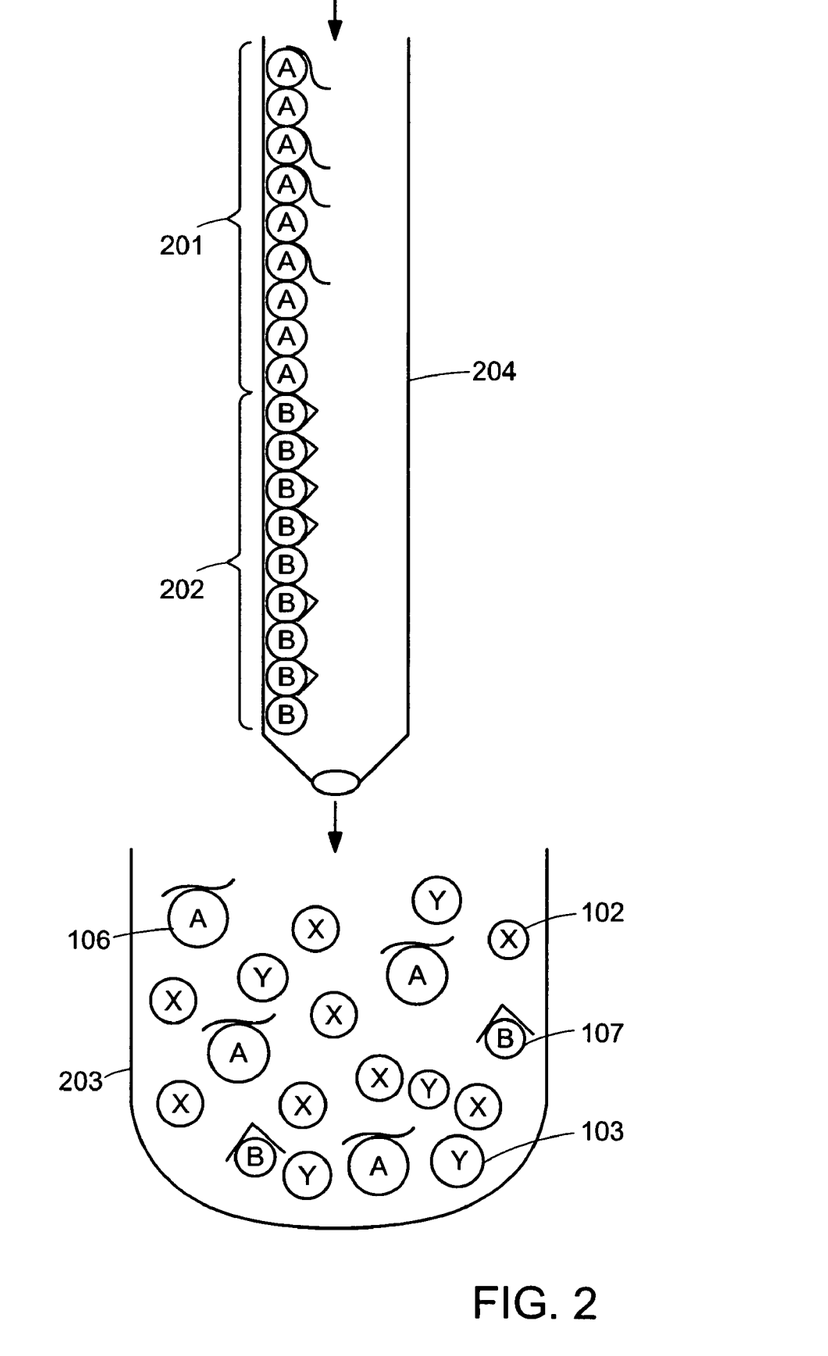
FIG. 2 shows schematically the effect after the materials in FIG. 1 are further treated to remove remaining uncomplexed aptamers.

Such an embodiment is illustrated in FIGS. 1 and 2. FIG. 1 illustrates schematically the operation of an embodiment of a method in accordance with the present invention at an intermediate stage after the addition of aptamers to an aliquot with a sample being analyzed. In this example, we are performing a quantitative assay for target proteins A and B, namely items 106 and 107 respectively, that occur in low abundance in a sample contained in a region 101, which is here a vessel such as an Eppendorf tube. Also in the sample in FIG. 1 are a number of proteins that are not of interest, namely X and Y, items 102 and 103 and 104, respectively. Also placed in the region is an aptamer 104 that is specific for protein A and an aptamer 105 that is specific for protein B. These aptamers are present in relatively larger abundance in the region than the target proteins, with the result that substantially all of proteins A and B in the region form complexes with their respective aptamer, and excess uncomplexed quantities of each of the aptamers for each of the target proteins remain in the sample.

FIG. 2 shows how the materials in FIG. 1 may be further treated to remove excess uncomplexed aptamer by affinity. In this example, a column 204 has each of the target proteins A and B immobilized in regions 201 and 202 respectively, in a manner known in the art. The immobilized proteins are present in sufficient abundance to form complexes with all uncomplexed aptamer molecules in the sample in vessel 101 of FIG. 1. In this manner when the sample from vessel 101 runs through the column 204, the uncomplexed aptamer molecules are removed from solution. In the resulting eluate mixture in collection region 203, all aptamer molecules present are bound to their respective target proteins.

Because the aptamers are nucleic acids, each aptamer in the collection region 203 can be assayed using a quantitative replicative procedure, such as a quantitative polymerase chain reaction procedure (QPCR). Because each aptamer assayed is complexed to its respective target protein in the collection region 203, the number of molecules of a given aptamer present in collection region 203 corresponds to the number of the corresponding target molecules in the same region and therefore in the sample.

G. Quantification of a Common Class Target Molecule and of Specific Target Molecules Within the Common Class.

A second preferred embodiment is directed towards quantification of a common class of molecules present in a sample. Specifically, the common class of target molecule is an antibody, more specifically the antibody class is IgE, and more specifically the target molecules are individual antigen-specific $IgE_x$ antibodies within the common class of IgE antibodies, for example $IgE_1$, $IgE_2$, $IgE_3$ ... $IgE_x$. Aptamers are selected with specificity for the $F_C$ constant region of the IgE class of antibodies. Other aptamers are selected with specificity for the $F_{AB}$ hypervariable regions of specific $IgE_x$ antibodies within the common class. Alternatively, antigens can be used as the molecules with specificity for the $F_{AB}$ hypervariable region of the antibody.

The aptamers specific for the $F_C$ constant region of the IgE target molecules are allowed to mix with all the IgE antibodies in a sample such that all the common class target molecules in the sample bind to the aptamers. The sample may be human blood, or blood serum, for example. Then, an aliquot of this sample mixture is applied to an affinity column containing immobilized $F_C$ constant region of IgE, permitting separation of all unbound aptamer remaining in the sample mixture. The eluate from this first column thus contains target IgE molecules only bound to aptamer. An aliquot of the eluate is then applied to a second affinity column containing immobilized aptamer or antigen specific for the $F_{AB}$ hypervariable region of a specific $IgE_x$ antibody. This second column permits removal of specific $IgE_x$ antibodies from the sample mixture, leaving all aptamer-bound IgE common class molecules in the eluate except those which bind the specific $IgE_x$ aptamer or antigen immobilized on the second column. Quantitative replicative procedures are then performed on aliquots of eluate from each of the first and second affinity columns, and the difference in quantification of aptamer determined for each eluate aliquot is used to determine the quantity of specific $IgE_x$ antibody.

In a similar preferred embodiment, the first target molecule is again a common class of molecules, specifically antibodies, more specifically the IgE class of antibodies, and more specifically individual $IgE_x$ antibodies within the IgE class. Aptamers are again selected for specificity to the constant region of the IgE class of antibodies, and other aptamers are selected for specificity to the hypervariable regions of specific $IgE_1$, $IgE_2$, $IgE_3$ . . . $IgE_x$ antibodies within the common class, or specific antigens are used. In this embodiment however, after allowing aptamer to mix and bind to the common class IgE antibodies in the sample, the first column is run simultaneously with the second column, but on two different aliquots from the same sample/aptamer mixture. Column one contains both constant region of IgE class antibody and aptamer or antigen specific for the hypervariable region of a specific $IgE_x$ antibody immobilized on the affinity column. Column two contains only immobilized constant region of IgE class antibody. Quantitative replicative procedures are then run on aliquots from the eluate of each of the two columns. The difference in quantification values of aptamer determined for each eluate is then used to determine the quantity of specific $IgE_x$ antibody originally present in the sample mixture.

Figure 3:
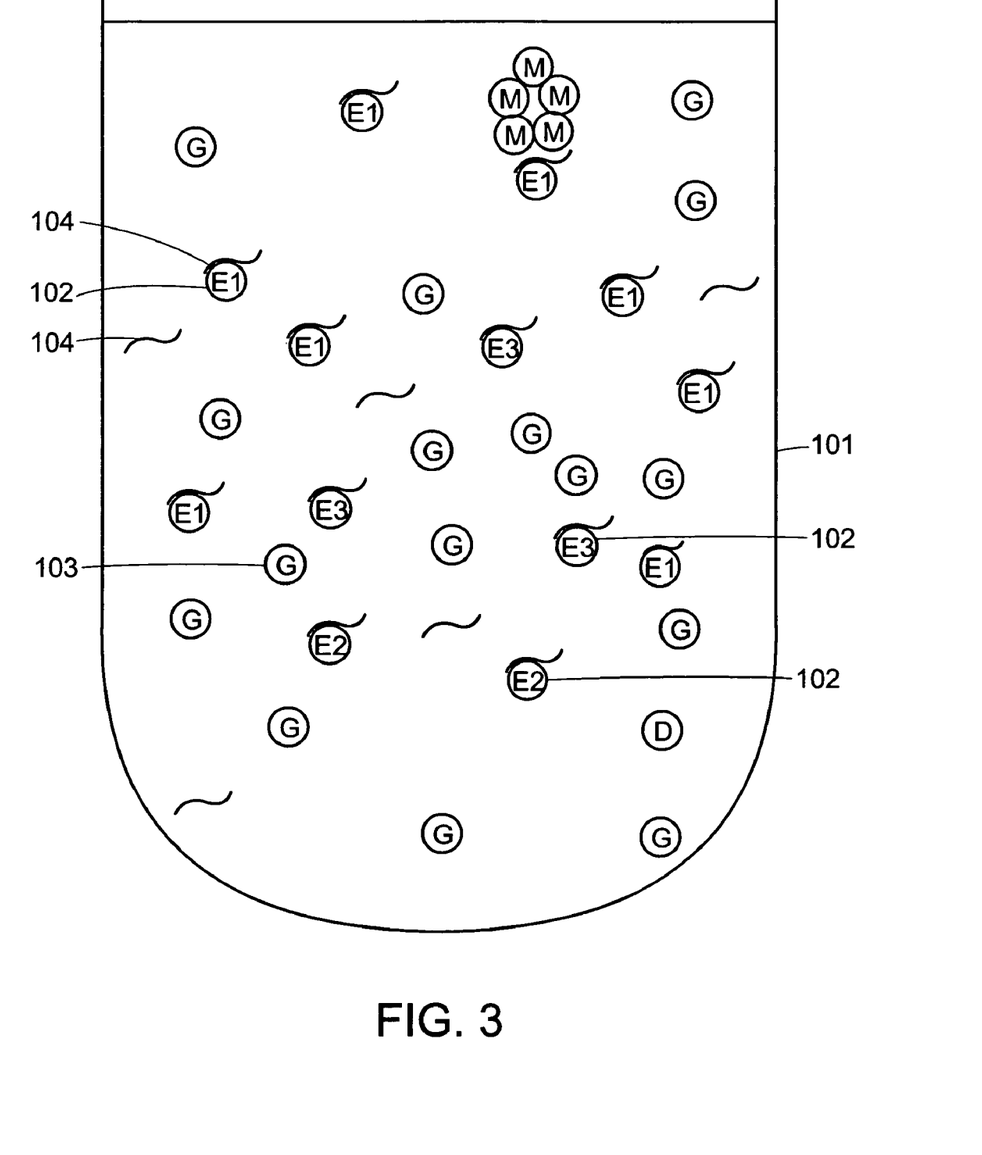
FIG. 3 illustrates schematically an intermediate stage after the addition of aptamers to a sample to determine the amount of different antibodies in the sample, the sample being analyzed to detect antibody-aptamer complexes in a common class mixture.

FIG. 3 relates to such an embodiment of the present invention, specifically for quantifying the antibody response of a subject to one or more antigens. The method of this embodiment relies on the fact that all antibody molecules of a given common class can be collected by virtue of sharing a common $F_C$ region, while all $IgE_x$ antibody molecules specific for a given antigen can be collected by virtue of affinity for that antigen. FIG. 3 illustrates schematically the operation of an embodiment at an intermediate stage after the addition of aptamers to a region with a sample being analyzed to form antibody-aptamer complexes in a common class mixture.

FIG. 3 shows a region 101, realized here as a vessel, in which there is included a sample of tissue (such as blood) from a subject having antibodies of several different common classes including IgE, item 102, symbolized by an E, IgG, item 103, symbolized by a G. Some of the IgE antibodies have specificity for a first antigen, and these IgE antibodies are shown as $E_1$ in FIG. 3. Some of the IgE antibodies have specificity for a second antigen, and these IgE antibodies are shown as $E_2$ in FIG. 3. Finally, some of the IgE antibodies have specificity for a third antigen, and these IgE antibodies are shown as $E_3$ in FIG. 3. To the vessel 101 has been added an aptamer 104 that binds generally to IgE antibodies regardless of the antigen for which each IgE antibody has specificity. Aptamer has been added in greater abundance than the IgE antibody 102, so that substantially all of the IgE antibodies have formed complexes with aptamer. The resultant mixture in FIG. 3 is referred to as a common class mixture. A measured amount of aptamer is added to the vessel, so that the unbound aptamer 104 provides an inverse measure of the amount of the common class of total IgE present in the subject.

Figure 4:
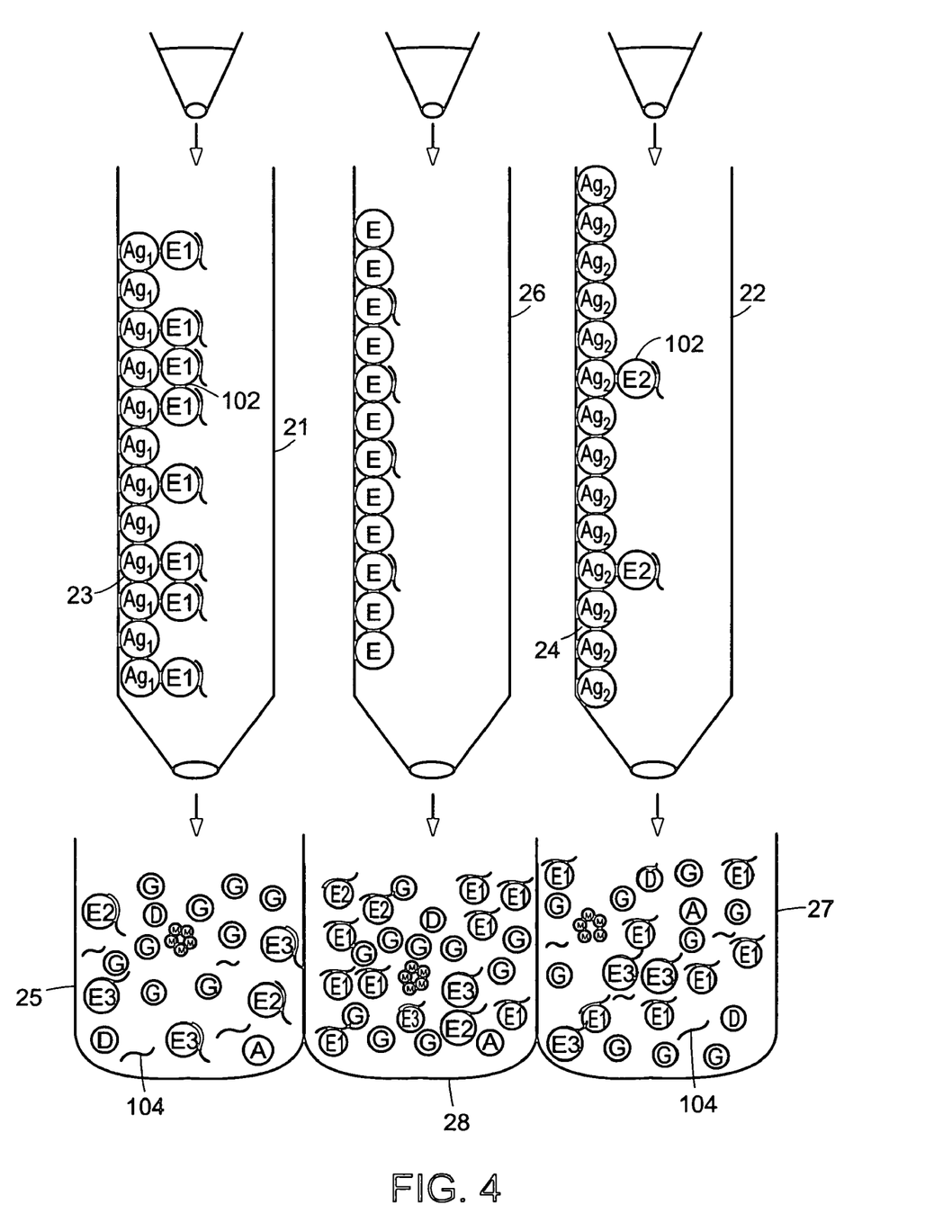
FIG. 4 shows schematically the separation of antigen-specific antibody-aptamer complexes from aliquots of the common class mixture.

FIG. 4 shows schematically the effect of separation, from aliquots of the common class mixture, of antigen-specific antibody-aptamer complexes. The first antigen 23 ($Ag_1$), namely the antigen for which $E_1$ antibody is specific, is immobilized in column 21. Similarly, the second antigen 24 ($Ag_2$), namely the antigen for which $E_2$ antibody is specific, is immobilized in column 22. The $F_C$ constant region of IgE is immobilized on column 26. A separate aliquot of the common class mixture of FIG. 3 is run through each of the columns 21 or 22. The effect of the first antigen in column 21 is to remove from the mixture only the $E_1$ antibody-aptamer complexes. Similarly, the effect of the second antigen in column 22 is to remove from the mixture only $E_2$ antibody-aptamer complexes. The effect of the immobilized Fc region of IgE in column 26 is to remove all unbound aptamer, leaving only $IgE_x$-bound aptamer in the eluate of collection chamber 28. If the common class mixture is run through columns 21 or 22, and the resultant flow-through is collected in a collection chamber 25 or 27, respectively, what remains is a mixture including the uncomplexed aptamer 104, antibody molecules of the same common class which lack specific affinity for the first or second antigens, and antibody of any other class which lack specific affinity for the antigen, these being collected along with the unbound aptamer.

Quantification of the specific antibodies $E_1$ or $E_2$ may be quantified in a number of different ways. In a first embodiment, uncomplexed aptamer 104 is removed from the common class mixture using a column, 26, with immobilized $F_C$ region of IgE. After removal of this uncomplexed aptamer, the total quantity of aptamer in the resulting column flow-through (eluate) in collection chamber 28, which in the mixture is complexed with all IgE, is a measure of total IgE concentration in the original common class mixture and therefore in the tissue sample. QPCR techniques are applied to determine the amount of aptamer and therefore of IgE.

Then, an aliquot of the eluate from either column 21 or 22 is applied to column 26. The amount of antibody-bound aptamer remaining in the eluate after application of sample aliquots to column 21 or 22, followed by column 26, is again determined using QPCR techniques. The difference between quantity of aptamer in this second eluate (from sequential application of sample to column 21 or 22 followed by column 26) and quantity of aptamer in the eluate of column 26 alone is attributable to $IgE_1$ or $IgE_2$ that has bound to its specific antigen in either column 21 or 22, and therefore is a measure of specific $IgE_1$ or $IgE_2$ antibody originally present in the sample.

Alternatively, an aliquot of the common class mixture can be applied to a column (not shown) having both immobilized IgE and specific antigen $IgE_x$, to bind both unbound aptamer and antigen-specific $IgE_x$ bound to aptamer. The difference by QPCR of aptamer in the eluate of this column and from a column having only bound IgE is a measure of the quantity of the $IgE_x$ present in the original common class mixture, and hence the tissue sample.

In another embodiment, a measurement is made directly on the antibody-aptamer that has remained bound to the immobilized specific antigen in each column 21 and 22. The column is eluted with a denaturing solution, and a QPCR assay may be performed on the eluate or a derived fraction of the eluate. For example, the column can be eluted using a buffer having a high or a low pH, and the eluate can be neutralized prior to a qualitative replicative assay. Thereupon, quantitative replicative procedure is performed such that the aptamer molecules which are complexed to the shared sites located in the $F_C$ region of a common class of antibody molecules can be accurately and repeatedly replicated by one or more nucleic acid polymerases or other enzymes of nucleic acid synthesis.

Prior to that replication, however, the mixture of all species within the common class is further fractionated by collecting the total number of antibody-aptamer complexes having a certain antigen specificity, as illustrated in FIG. 3. This is possible because the antigen-specificity is determined by amino acid residues at the other end of the antibody molecule, the $F_{AB}$ region. An aliquot of the initial mixture of the tissue, for example, blood (including a blood fraction such as plasma or serum) is affinity purified by virtue of affinity for molecules in a purified preparation of the antigen. This can be achieved as illustrated in FIG. 4.

The number of cycles required for sufficient replication of the aptamer molecule is a measure of its level of abundance.

H. Pluralities of Fractions Obtained in the Method

Multiple levels of pluralities can be utilized. A tissue sample can be fractioned prior to use, for example, blood cells and clotting proteins can be removed, producing derivative fractions such as serum and plasma. Further, each of several aliquots of the common class mixture of FIG. 3 containing aptamer bound to all of the molecules of a common class, and excess aptamer, can be further fractionated to obtain the subclasses of molecules having antigen-binding determinants for each of a plurality of antigens. For example, a tissue sample of a subject can first be exposed to an aptamer specific for IgE, then aliquots of the resulting common class mixture can be exposed, for example, to each of a dust mite antigen, to an antigen of cat saliva, and to an antigen found in human collagen.

In each of these antigen-based purifications, the aptamer-antibody complex that binds to the antigen can be isolated, and the aptamer can be subjected to a replicative procedure to quantify the amount of the complex so isolated. The result can be compared with the total aptamer present in the original mixture in FIG. 3, with the amount that binds and that fails to bind the antigen and is collected as a "flow-through" of eluate from the bottom of each column. Thus, in the instance that only a small amount of complex binds to a column, an accurate and significant reading of this small bound amount can be made using the replicative procedure. If, however, a large amount binds to the antigen, an accurate assessment of the amount in the eluate that flows into a collection chamber 25 in FIG. 4 can be obtained. All the values can be compared to normative data obtained from other subjects, or from earlier samples obtained from the same subject, or from comparison to the amount of the common class mixture bound to IgE. A plurality of different antigens can be used simultaneously to assay the sample or samples from the subject. Different family members can be tested, and samples can be obtained over the time course of administration of a particular drug or drugs.

What is claimed is:

1. A method for quantitatively assaying a target molecule in a first sample, comprising:
   (a) adding to the first sample, a preparation of a nucleic acid aptamer specific for the target molecule;
   (b) allowing substantially all of the target molecule in the first sample to bind with the aptamer to form a complex consisting of aptamer and target molecule;
   (c) separating unbound aptamer from the first sample by contacting the sample of step (b) with immobilized ligand, thereby binding the ligand to unbound aptamer, so as to recover a second sample of aptamer bound to target molecule; and
   (d) using a quantitative replicative procedure comprising a replicative polymerase reaction to determine a quantity of aptamer specific for the target molecule in the second sample and therefore related to the concentration of target molecule in the first sample.

2. A method according to claim 1, wherein the nucleic acid aptamer is selected from the group consisting of single-stranded DNA, double-stranded DNA, single-stranded RNA, double-stranded RNA and chemical modifications thereof.

3. A method according to claim 1, wherein the target molecule is present in the sample at a molar concentration less than its dissociation constant with respect to the aptamer.

4. A method according to claim 1, wherein the target molecule is present in the sample at a molar concentration equal to or greater than its dissociation constant with respect to the aptamer.

5. A method according to claim 1, wherein the target molecule is a low abundance molecule.

6. A method according to claim 1, where the target molecule includes a biological macromolecule.

7. A method according to claim 6, wherein the biological macromolecule is selected from the group consisting of a protein, a lipid, a polysaccharide or combinations thereof.

8. A method according to claim 1, wherein the target molecule includes a small organic molecule.

9. A method according to claim 8, wherein the small organic molecule is selected from the group consisting of antibiotics, vitamins, steroids, and pesticides.

10. A method according to claim 1, wherein the target molecule includes an inorganic molecule.

11. A method according to claim 10, wherein the inorganic molecule is a metal.

12. A method according to claim 11, wherein the metal is selected from the group consisting of metal ions, metal oxides, and metal complexes.

13. A method according to claim 1, wherein the first sample is obtained from an animal subject.

14. A method according to claim 13, wherein the first sample is selected from the group of tissues consisting of organ tissue, muscle tissue, bone tissue, connective tissue, fetal tissue, and placental tissue.

15. A method according to claim 1, wherein the first sample is a biological fluid selected from the group consisting of blood, lymph, urine, sputum, joint fluid, spinal fluid, and saliva.

16. A method according to claim 1, wherein the first sample is an environmental sample.

17. A method according to claim 16, wherein the environmental sample is obtained from a source selected from the group consisting of plants, water, food, beverages and industrial waste.

18. A method according to claim 1, wherein the immobilized ligand is immobilized on a support matrix selected from the group consisting of resins, beads, magnetic beads, gels, cellulose and silica.

19. A method according to claim 1, wherein the immobilized ligand is immobilized on an affinity column.

20. A method according to claim 1, wherein the quantitative replicative procedure is a quantitative polymerase chain reaction.

21. A method according to claim 1, wherein determining the quantity of aptamer bound to the target molecule further includes denaturing the aptamer so as to separate the nucleic acid from the target molecule.

22. A method according to claim 21, wherein oligonucleotide primers are added to the sample after denaturing the aptamer from the target molecule.

23. A method according to claim 22, wherein determining the quantity of aptamer includes determining a number of replicative cycles.

24. A method according to claim 6, wherein the target molecule is an antibody.

25. A method according to claim 24, wherein the target molecule includes IgE.

26. A method according to claim 1, wherein the target molecule includes a plurality of antibody molecules belonging to different subclasses characterized by a difference in the hypervariable region of each antibody.

27. A method according to claim 1, wherein the target molecule is a subclass of an antibody having a characteristic hypervariable region.

28. A method according to any one of claims 24–25 or 27, wherein the aptamer binds to a constant region of the antibody and wherein the immobilized ligand is the constant region of the antibody for removing unbound aptamer from the sample.

29. A method according to claim 27, wherein the second sample contains antibody-bound aptamer, the second sample being divided into a plurality of aliquots, and a first aliquot of the second sample being assayed using a quantitative replicative procedure to determine quantity of antibody in the first sample.

30. A method according to claim 29, further comprising:
  (a) contacting a second aliquot of the second sample with an immobilized ligand for binding an antibody with a first hypervariable region; wherein the antibody with a first hypervariable region is a target molecule in the first sample;
  (b) recovering a third sample containing the aptamer bound to target molecule excluding the antibody with the first hypervariable region;
  (c) assaying the aptamer concentration in the third sample using the quantitative replicative procedure, so as to determine a difference in a quantity of aptamer in the second sample and the third sample; and
  (d) determining a quantity of the antibody with the first hypervariable region in the first sample from the difference.

31. A method according to claim 29, further comprising:
  (a) contacting a plurality of aliquots of the second sample with a plurality of immobilized ligands wherein each ligand is immobilized by attachment to a substrate in a single chamber, each immobilized ligand having a specificity for an antibody with a different hypervariable site;
  (b) recovering a third sample containing the aptamer bound to target molecule excluding the antibody bound to immobilized ligand;
  (c) assaying the aptamer concentration in the third sample using the quantitative replicative procedure, so as to determine a difference in a quantity of aptamer in the second sample and the third sample; and
  (d) determining a quantity of the antibody with the hypervariable region in the first sample from the difference.

32. A method according to claim 30, wherein the ligand is a specific antigen.

33. A method according to claim 1, wherein the ligand is a reagent having the aptamer-binding characteristics of the target molecule.

34. A method according to any one of claims 30 or 31, wherein the antibody is IgE.

35. A method according to claim 26, wherein the aptamer binds to a constant region of the plurality of antibody molecules and wherein the immobilized ligand is the constant region of the antibody molecules for removing unbound aptamer from the sample.

36. A method according to claim 31, wherein each ligand is a specific antigen.

* * * * *